United States Patent [19]

Strong et al.

[11] Patent Number: 5,423,847
[45] Date of Patent: Jun. 13, 1995

[54] SAFE LANCET INJECTOR

[75] Inventors: Bernard Strong, Tarzana, Calif.; Robert Oringer, Hampstead, Canada

[73] Assignee: AMG Medical, Inc., Montreal, Canada

[21] Appl. No.: 225,309

[22] Filed: Apr. 8, 1994

Related U.S. Application Data

[63] Continuation-in-part of Ser. No. 7,339, Jan. 21, 1993, Pat. No. 5,324,303.

[51] Int. Cl.⁶ .............................................. A61B 17/32
[52] U.S. Cl. ...................................... 606/182; 606/181
[58] Field of Search ...................... 606/181, 182, 183; 604/117, 136, 157; 128/770

[56] References Cited

U.S. PATENT DOCUMENTS

| | | |
|---|---|---|
| 3,358,689 | 12/1967 | Higgins . |
| 4,139,011 | 2/1979 | Benoit et al. . |
| 4,203,446 | 5/1980 | Hofert et al. . |
| 4,356,822 | 11/1982 | Winstead-Hall . |
| 4,449,529 | 5/1984 | Burns et al. . |
| 4,469,110 | 9/1984 | Slama . |
| 4,503,856 | 3/1985 | Cornell et al. ...................... 606/182 |
| 4,517,978 | 5/1985 | Levin et al. ........................... 606/182 |
| 4,527,561 | 7/1985 | Burns . |
| 4,677,979 | 7/1987 | Burns . |
| 4,738,261 | 4/1988 | Enstrom . |
| 4,759,363 | 7/1988 | Jensen . |
| 4,817,603 | 4/1989 | Turner et al. . |
| 4,889,117 | 12/1989 | Stevens . |
| 4,895,147 | 1/1990 | Bodicky et al. . |
| 4,976,724 | 12/1990 | Nieto et al. . |
| 4,990,154 | 2/1991 | Brown et al. . |
| 5,074,872 | 12/1991 | Brown et al. . |
| 5,147,375 | 9/1992 | Sullivan et al. ...................... 606/182 |
| 5,196,025 | 3/1993 | Ranalletta et al. ................... 606/182 |
| 5,269,799 | 12/1993 | Daniel ................................. 606/182 |
| 5,304,193 | 4/1994 | Zhadanov ........................... 606/182 |
| 5,318,583 | 6/1994 | Rabenau et al. .................... 606/182 |
| 5,318,584 | 6/1994 | Lange et al. ........................ 606/181 |
| 5,324,303 | 6/1994 | Strong et al. ....................... 606/181 |

*Primary Examiner*—Ralph A. Lewis

[57] ABSTRACT

Disclosed is a lancet injector for use with a lancet and an isolating platform to obtain blood samples for diagnostic purposes in a very safe and accurate manner. This lancet injector makes use of two elastomeric bands to push the lancet forwards and to rapidly withdraw the needle from the skin. The lancet injector also has an interlocking mechanism which completely precludes a lancet from being used more than once and thus obviates accidental misuse which could cause cross-contamination between patients. It further has a mechanism which allows the lancet itself to dislodge the platform thereby causing it to automatically jump forward in front of the needle as it collapses and thus to hood the needle and grip the main body of the lancet. It may also be provided with a window in its housing, through which a three color display panel can be viewed. When the lancet injector is ready for loading, a color is displayed, thus indicating that the injector has been emptied and may now be loaded and then cocked. When cocked, another color is displayed, thus indicating that the injector is ready to be fired. After firing, a third color is displayed to give warning signal that the ejector contains a lancet which has been used and should immediately be ejected. The third color display remains locked until the lancet is completely ejected.

16 Claims, 7 Drawing Sheets

SAFE LANCET INJECTOR

CROSS-REFERENCE

This application is a continuation-in-part of application Ser. No. 08/007,339, filed on Jan. 21, 1993, now U.S. Pat. No. 5,324,303.

BACKGROUND OF THE INVENTION a) Field of the Invention

The present invention relates to an improved blood sampling device also known in the trade as a "lancet injector", that can be used in combination with a lancet and an isolating platform to obtain blood samples for diagnostic purposes in a very safe and accurate manner.

The invention also relates to the combination of such a lancet injector with a lancet and an isolating platform especially adapted for use therewith.

b) Brief Description of the Prior Art

Lancets are well known devices commonly used in the medical field to make small punctures in a patient's skin in order to obtain samples of blood. Lancets usually comprise an elongated plastic body from which projects a sharpened metal needle covered by a protective cap that is removed before use of the needle to puncture the skin (see, by way of non-restrictive example, U.S. Pat. No. 3,358,689 to HIGGINS).

Lancet injectors are also well known devices that are used to "fire" or project a lancet toward the skin of a patient in order to puncture the same in an accurate, standardized and consistent manner.

Such devices have originally been devised for use by the patients themselves, who have to puncture their own skin on a regular basis and are afraid or reluctant to do so "manually". However, they are now commonly used by professional medical staff, essentially because they make the duration and depth of penetration of the lancet needle through the skin very short and small and serve to shield the patient from viewing the actual skin piercing act, and thus to minimize pain and trauma associated with the process.

In the recent years, numerous patents have been granted on lancet injectors which are of different and improved structures. All these known lancet injectors use metallic or leaf springs to push the lancet forward upon actuation and then retract it immediately in order to minimize pain sensation (see, for example, U.S. Pat. Nos. 4,203,446; 4,469,529; 4,527,561; 4,677,979 and 4,889,117).

Some known lancet injectors are also provided with means, usually in the form of a screwable ring or separable multiple sized adaptor caps, to control and adjust the depth of penetration of the needle of the lancet (see, for example, U.S. Pat. Nos. 4,469,110 and 4,895,147).

Some other known lancet injectors are provided with means for allowing ejection of the lancet after use without having to seize it with the fingers to do so. Such is achieved either by use of mechanical ejecting means (see U.S. Pat. No. 4,976,724) or by use of a separate disposable isolation cap operatively connected to the lancet in such a manner as to act as a protective hood for its needle (see U.S. Pat. Nos. 4,990,154 and 5,074,872). The basic idea behind this last generation of lancet injectors is essentially to make them safer in use by the medical staff who is more and more concerned with the risk of disease transmission in the case of accidental puncture with a used lancet and resultant exposure to contamination through the trace of blood left on the used lancet.

In Applicant's U.S. Pat. No. 5,324,303 referred to hereinabove, there is disclosed a combined, single-use, disposable lancet and multi-function cap, in which the multi-function cap is so devised as to be useful in the following four separate and distinct functions.

First function: The multi-function cap serves as a protective cap (or sealed barrier) to keep the sharp needle of the lancet protected and sterile after moulding and prior to being twisted off to reveal the needle for actual use.

Second function: The multi-function cap serves as an isolation cap (or physical intermediary) when the lancet is being used with a lancet injector such that no physical part of the actual injector itself may come into contact with the target area of the patient's skin from which blood is to be drawn. Only the multi-function cap makes physical contact with the target area of the patient's skin from which blood is to be drawn.

Third function: The multi-function cap serves as a means of controlling depth of penetration when the lancet is being used with a lancet injector such that the user has variable options of depth to which the lancet may be allowed to penetrate the skin.

Fourth function: The multi-function cap serves as a protective cap (or locking hood) to cap and permanently lock the used sharp lancet needle "within" the cap immediately upon ejection and discarding of the used lancet, thus serving to protect users and medical professionals against the risk of accidental finger puncture once the lancet has been used (fired). Simultaneously, the multi-function cap serves to prevent the lancet from being fired accidentally for a second time.

The fact that the multi-function cap is not only acting as a protective cap to keep the needle sterile before use, but also as an isolation cap, a depth penetration barrier and a locking needle hood, is of a great interest as it eliminates the need for an extra isolation cap and it economizes both in manufacturing cost and in required amount of plastic material.

In former U.S. Pat. No. 5,324,303, a blood sampling lancet injector is also disclosed, for use with the above mentioned combined lancet and multi-function cap. This lancet injector is devised to reduce the danger of accidental finger-stick from a "used" blood contaminated lancet needle, thanks to the presence of ejection means which automatically ejects the lancet in concert with the multi-function cap that firmly grips onto the lancet at a predetermined position where it may acts as a protective locking hood for the needle after the injector has been "fired" and the used lancet is ejected to be discarded.

Thanks to the multi-function cap used therewith, the blood sampling lancet injector also allows for easy regulation of the depth of skin penetration in a positive and reliable manner for the purpose of obtaining a blood droplet or sample of optimum volume while simultaneously serving to diminish as much as possible patient discomfort.

In this connection, it is known that normal average desirable penetration to produce sufficient blood for glucose content measuring purposes as required for instance by most diabetic patients, is around 0.040". For young children, a penetration 0.025" to 0.030" is sufficient and provides less discomfort while for some adults who have a thicker than usual epidermis, up to 0.090" may be needed to produce an ample blood droplet. The invention disclosed in U.S. Pat. No. 5,324,303 provides for all penetration depths within these two extremes with a lancet having just one given needle length, the required depth being easily adjusted in a very reliable manner by mere rotation of a depth indicator that forms part of the multi-function cap and is provided with an easy-to-read scale giving different comfort depth values, in order to reduce as much as possible discomfort.

The blood sampling lancet injector disclosed in U.S. Pat. No. 5,324,303 is also interesting as compared to the previous lancet injectors in that it eliminates the use of metallic springs, and uses instead an elastomeric band which is suitably restrained at four points so as to provide a unique two-way, well cushioned prime mover providing both for very rapid skin piercing and speedy withdrawal of the needle, which serve to minimize patient discomfort.

Thus, U.S. Pat. No. 5,324,303 discloses a blood sampling lancet injector which incorporates each and all of the above mentioned features and thus:

- is much less complicated than the prior art devices which require the use of metallic springs that are far more costly than the elastomeric band used herein;
- is much safer than the prior art devices which do not provide for disposable isolation caps, the injector not only obviating cross-contamination but also allowing for instant regulation of the depth of skin penetration and protective hooding and locking of the needle after use to eliminate the possibility of "second firing" without employing any extra components; and
- is much less expensive to manufacture than the prior art devices which, for most, require costly assembly operations that may include sonic welding, gluing and/or screwing, the invention, in complete contrast, providing for rapid low cost assembly with all components suitably shaped to rapidly click together either by hand or a robotic assembly machine.

OBJECTS OF THE INVENTION

A first object of the present invention is to provide a safe lancet injector for use with a disposable lancet and multi-function cap (hereinafter called "isolating platform") of the substantially same type and function as the combined lancet and multifunction cap disclosed in Applicant's former U.S. Pat. No. 5,324,303, which injector has a plurality of additional features as compared to the lancet injector disclosed in said former application.

These additional features which can be used alone or in combination with each other are as follows:

1. INTERLOCK

The lancet injector according to the present invention has an improved interlocking mechanism which completely precludes a lancet from being used more than once and thus obviates accidental misuse which could cause cross-contamination between patients. This mechanism includes a pair of programmed angulated slots made in the chassis of the injector to automatically position the essential operating elements in the correct location at the desired time in each sequential cycle and a memory mechanism which senses whether or not the injector contains a used lancet.

2. MODE WINDOW

The lancet injector according to the invention may be provided with window in its housing through which a three color display panel can be viewed. When the lancet injector is ready for loading, a color (like white, for example) is displayed, thus indicating that the injector has been emptied and may now be loaded and then cocked. When cocked, another color (like green) is displayed, thus indicating that the injector is ready to be fired. After firing, a third color (like red) is displayed to give warning signal that the ejector contains a lancet which has been used and should immediately be ejected. The red display remains locked until the lancet is completely ejected. Then the mechanism may restore itself to rest and simultaneously change the display back to white.

3. SAFETY BUTTON

The lancet injector according to the invention may also be provided with a transparent shield for protecting the firing button against inadvertent operation in such a manner that this button can only be operated by a meniscus being formed on the user's fingertip which is simply effected by deliberate finger pressure being applied to both button and shield.

4. ELASTOMERIC BANDS

Like in U.S. Pat. No. 5,324,303, the lancet injector according to the present invention makes use of an elastomeric band to push the lancet forwards. However, instead of using one band only, it uses two or them, the second band serving three distinct functions: firstly, to automatically return the ejector knob; secondly, to rapidly withdraw the needle from the skin and thirdly, to provide the requisite tension to ensure that the axles of the ejector accurately follow the programmed angular slots provided in chassis of the injector. As a result of this major change, it has been possible to redesign the shaft of the injector so as to substantially increase the all important speed of penetration. Now, the main elastomeric band only serves to effect the forward or injection motion and to tension the safety button, but not to withdraw the needle from the skin. No metallic springs are used.

5. HOLDING OF THE NEEDLE

In U.S. Pat. No. 5324,303, a double acting timed ejection of the lancet and platform was provided. In the lancet injector according to the invention, means are provided to allow the lancet itself to dislodge the platform thereby causing it to automatically jump forward in front of the needle as it collapses to thus hood the needle and grip the main body of the lancet.

Another object of the invention is to provide the combination of the improved safe lancet injector disclosed hereinabove with a lancet and isolating platform that are so-devised as to meet all the functions of the former device, including, in particular:

- a structure which requires the use of metallic springs that are far more costly than the elastomeric band used herein;
- a structure which is much safer and efficient than the prior art devices, the invention not only obviating cross-contamination, but also allowing for instant regulation of the depth of skin penetration and protective holding and locking of the needle after use to eliminate the possibility of "second firing" without employing any extra component; and
- a structure which is much less expensive to manufacture than the prior art devices, because it provides for rapid low cost assembly with all components suitable shaped to rapidly click together either by hand or a robotic assembly machine.

SUMMARY OF THE INVENTION

In accordance with the invention, there is provided a lancet injector for use with a lancet and an isolating platform through which the lancet passes when it is projected by the injector.

This lancet injector comprises a chassis (a) having:
- a longitudinal axis;
- a front open end hereinafter called "mouth" on which the isolating platform can be detachably fixed; and
- a rear end.

This chassis defines an elongated passage opening into the mouth and comprises a longitudinal front slot and a longitudinal rear slot both opening into the passage, these two slots being aligned.

A shaft (b) is slidably mounted in a non-rotatable manner within the passage. This shaft has:
- a forward end integrally connected to a launching socket in which the lancet to be injected is detachably insertable;
- a first abutment at a first distance rearward the launching socket;
- a leaf spring at a second distance rearward the abutment, this leaf spring projecting forwardly outwardly from the shaft and being lockingly engageable with a stop provided in the rear slot of the chassis when tile shaft is moved rearwardly within the passage; and
- a rearward end defining a second abutment.

A first elastomeric band (c) is held under slight tension between the second abutment of the shaft and a first elastomeric band attachment point provided on the chassis rearward the mouth of the same.

A lancet ejector (d) is slidably mounted in a non-rotatable manner within the passage of the chassis between the mouth of the same and the first abutment of the shaft. This lancet ejector comprises:
- a forwardly projecting stem that is slidably movable within the launching socket through a rear opening provided in the same;
- an operating knob projecting out of the chassis through an elongated opening provided in the same opposite to the front slot; and
- a small hook opposite to the knob, this hook being slidably engageable into the front slot of the chassis.

A second elastomeric band (e) is held under slight tension between the lancet ejector and a second elastomeric band attachment point provided on the chassis forward the rear end of the same.

A slide member (f) is slidably mounted onto the chassis so as to extend longitudinally over the front and rear slots of the chassis when the member is slid forward and rearward. This slide member comprises:
- a resilient front tip that is engaged by the hook of the ejector when this ejector moves from a maximum forward position to the rear;
- a lower rib that projects downwardly and is slidably engaged into the rear slot of the chassis; and
- a rear edge.

An actuating button (g) is slidably mounted at the rear end of the chassis so as to be movable along the longitudinal axis of said chassis. This button having a front surface that extends close to the rear edge of the slide member when the shaft is pushed rearwardly within the passage and the leaf spring is lockingly engaged with the stop in the rear slot in front of the lower rib of said slide member.

Of course, a housing (h) which is preferably made of two clippable half-parts, encloses all the above components except for the mouth of the chassis, the knob of the ejector and the actuating button.

In use, the following steps are carried out. First of all, the lancet injector is loaded by manually inserting the lancet into the launching socket while pressing on the knob of the ejector to deflect the adjacent shaft and thus prevent it from moving rearward.

Secondly, the injector is cocked by pushing rearwards the knob of the ejector bearing on the abutment of the shaft so as to push rearwards this shaft until its leaf spring is lockingly engaged with the stop in the rear slot of the chassis, such a pushing also causing the slide member to move freely rearward behind the leaf spring engaged with the stop in the rear slot, and the first elastomeric band to tension.

Thirdly, the injector may be fired by pressing forward onto the actuating button, such a pressing causing the slide member to move forwards and its lower rib to disengage the leaf spring and thus to release the shaft that is projected forwardly and then rearwardly rapidly under the action of the first and second elastomeric bands, such a movement causing in turn the lancet in the launching socket to move out of the mouth of the chassis past the isolating platform and to penetrate for a very short period of time in the skin of a patient bearing onto this isolating platform.

Fourthly, the lancet may be injected from the injector by pushing forwards the lancet ejector until the lancet falls out of the mouth of the chassis, the ejector and the slide member hooked by the same being then moved back to their original position (see the first step hereinabove) under the action of the second elastomeric band.

In accordance with a particularly preferred embodiment of the invention, the chassis (a) has two opposite sidewalls that extend bilaterally and symmetrically on both sides of its longitudinal front slot and elongated opening. Each of the sidewalls comprises an angulated slot that extends forwardly at a sight angle towards the front slot. This angulated slot is of substantially the same length as the front slot and provided with a notch at substantially mid-length, that extends in a direction opposite to the elongated opening. Moreover, the lancet ejector (d) comprises two opposite pins that extend transversally to the stem and are slidably engaged into the angulated slots of the chassis, respectively.

This particularly preferred embodiment is interesting in that:
- during the loading step, the pressure exerted on the knob causes the pins to engage the notches made in the angulated slots of the chassis and be locked therein;
- during the cocking step, the angulated slots cause the lancet ejector to move away from the front tip of the slide member and thus to avoid any interference with the same until the injector is fired;
- during the firing step, the angulated slots cause the lancet ejector to move toward the front tip of the slide member and its hook to engage said front tip rearwardly of the same and to push said slide member forwards; and
- during ejecting step (iv), the angulated slots cause the hook of the ejector to deflect the front tip of the slide member and to pass in front of the same, thereby causing the ejector to push back the slide member when it moves rearwards under the action of the second elastomeric band.

As can be appreciated from the above description, the lancet injector according to the invention incorporates two elastomeric bands instead of one serving three distinct functions i.e. firstly, to automatically return the lancet ejector secondly, to rapidly withdraw the needle from the skin; and thirdly, to provide the requisite tension to ensure that the pins of the ejector accurately follow the angulated slots preferably provided in the chassis. This major change permits to substantially increase the speed of penetration. The main elastomeric band only serves to effect the forward or injection motion and to tension the actuating button but not to withdraw the needle from the skin.

In the particularly preferred embodiment of the invention disclosed hereinabove, the chassis incorporates a pair of angulated slots which automatically position the essential operating elements in the correct location at the desired time in each sequential cycle. These slots coupled with the memory mechanism provided by the slide member, which senses whether or not the injector contains a used lancet, completely precludes a lancet from being used more than once and thus obviates accidental misuse which could cause cross-contamination between patients.

In accordance with another preferred embodiment of the invention, the actuating button (g) is slidably mounted into a tubular safety shield attached to the housing at the rear end of the chassis. This safety shield is of such a length that only a meniscus formed on a user's fingertip pressed onto the shield may push the actuating button to such an extent as to cause the slide member to disengage the leaf spring and thus to fire the injector.

In accordance with a further preferred embodiment of the invention, the slide member (f) has an upper surface opposite to its lower rib, which comprises a front portion of a first color, a medium portion of a second color and a rear section of a third color. Then, the housing (h) has a window opening onto the upper surface of the slide member. This window opening is advantageously positioned with respect to the chassis so that:

when the lancet injector is in its loading position, the second color is displayed through the window;

when the lancet injector is in locked position at the end of cocking step, the first color is displayed through the window, thereby indicating that the injector is ready to be fired; and when the lancet injector has been fired but the lancet has not been ejected yet, the third color is displayed through the window, thereby giving a warning signal that the ejector contains a used lancet which should immediately be ejected. This third color display remains locked until the lancet is ejected and the mechanism restores itself to rest at which time it changes back to first color.

In accordance with another aspect of the invention, there is provided a combination of the lancet injector disclosed hereinabove with a lancet and an isolating platform through which the lancet passes when it is projected by the injector.

In this combination, the lancet comprises:
an elongated body of a given diameter that is snugly insertable into the launching socket of the lancet injector; and
an axial needle embedded into the body, this needle having a sharp end projecting out of the body at a given distance away from one end of the same.

The isolating platform comprises:
a front plate that extends transversally to the mouth of the chassis when the isolating platform is connected thereto, the plate having a given thickness and a central through-hole of a diameter smaller than the one of the body of the lancet so as to stop this body while allowing the needle of the lancet to pass through the through-hole and to project out of the plate when the injector is fired; and
a fixation sleeve coaxial to the plate and sized to snap onto the mouth of the chassis so as to detachably connect the isolating platform to this mouth.

As can be appreciated, proper rotational selection of the thickness of the plate of the isolating platform permits to adjust the depth of penetration of the sharp end of the needle into the skin of the patient when the lancet injector is fired.

In accordance with a preferred embodiment of the invention, the one end of the body of the lancet where the sharp end of the needle projects out, has at least one radially extending section that projects in the same direction as the sharp end of the needle, and the front plate of the isolating platform has one surface hereinafter called "inner surface", which faces the radially extending section of the body when the lancet is inserted in the launching socket and the platform is snapped onto the mouth of he ejector. This inner surface has at least two different radial sections that project at different distances away from an average plane parallel to the plate. As a result, proper adjustment of the position of the isolating platform by rotation of the same about the mouth of the lancet injector relative to the lancet when the same is inserted into the launching sleeve, allows the radially extending section projecting from the one end of the body to be brought into alignment with a preselected radial section of the inner surface of the front plate of the platform and thus to control the depth of penetration of the lancet.

BRIEF DESCRIPTION OF THE DRAWINGS

The invention and its numerous advantages listed hereinabove will be better understood upon reading the following non-restrictive description of a preferred embodiment thereof, reference being made to the accompanying drawings in which.

DESCRIPTION OF A PREFERRED EMBODIMENT OF THE INVENTION

The lancet injector 1 according to the invention as shown in the accompanying drawings is intended to be used with a lancet 3 and an isolating platform 5 through which the lancet passes when it is projected by the injector, in order to obtain blood samples for diagnostic purposes.

As is better shown in FIGS. 1 and 2, the lancet injector 1 comprises an elongated chassis 7 which has a longitudinal axis, a rear end 9 and a front open end 11 hereinafter called "mouth", on which the isolating platform 5 can be detachably fixed via a shelf-defining ring 13, whose structure will be disclosed in greater detail hereinafter. The chassis 1 defines an elongated passage 15 opening into the mouth 11 and comprises a longitudinal front slot 17 and a longitudinal rear 19 slot that extends in line on its top surface and both open into the passage. The chassis also comprises a first pair of opposite sidewalls 21 that extend bilaterally and symmetrically on both sides of the longitudinal front slot 17 and together define an elongated opening 15' in the chassis, opposite to the top surface of the same. Each of the sidewalls 21 comprises an angulated slot 23 that extends forwardly at a slight angle towards the front slot. As is shown, the angulated slots 23 are of substantially the same length as the front slot 17 and each provided with a notch 25 at substantially mid-length, which extends towards the top surface of the chassis, i.e. in a direction opposite to the elongated opening 15'.

The lancet injector 1 also comprises a shaft 27 slidably mounted in a non-rotable manner within the passage 15. This shaft has a forward end integrally connected to a launching socket 29 in which the lancet to be injected is detachably insertable. The shaft 27 also has a first abutment 31 at a first distance rearward the launching socket 29, an integral leaf spring 33 at a second distance rearward the abutment 31 and a rearward end defining a second abutment 35. As is shown, the leaf spring 33 projects forwardly outwardly from the shaft 27 and is sized to be lockingly engageable with a stop 20 provided in the rear slot 19 of the chassis 7 when the shaft is moved rearwardly within the passage 15.

A first elastomeric band 37 is held under slight tension between the second abutment 35 of the shaft and a first elastomeric band attachment point 39 defined by the upper portions of the front edges of another pair of opposite sidewalls 39 projecting from the top surface of the chassis 7 rearward the first pair of sidewalls 21 of the same.

The lancet injector 1 further comprises a lancet ejector 43 slidably mounted in a non-rotatable manner within the passage 15 of the chassis 7 between the mouth 11 of the same and the first abutment 31 of the shaft 27. This ejector 43 comprises a forwardly projecting stem 45 that is slidably movable within the launching socket 29 through a rear opening 47 provided in the same (see the cutout portion in the socket 29 in FIG. 2). The ejector 43 also comprises an operating knob 49 projecting out of the chassis through the elongated opening 15' provided in the same, opposite to the front slot 17. The ejector 43 further comprises a small hook 51 that is opposite to the knob 49 and slidably engageable into the front slot 17 of the chassis, and two opposite axles or pins 53 that extend transversally to the stem 45 and are slidably engaged into the angulated slots 23 of the chassis, respectively.

A second elastomeric band 55 is held under slight tension between the lancet ejector 43 and a second elastomeric band attachment point 57 defined by the lower portions of the rear edges of the other sidewalls 41 of the chassis 7, at a given distance forward the rear end of this chassis.

The lancet injector 1 further comprises a slide member 59 slidably mounted onto the chassis 7 so as to extend longitudinally over the front and rear slots 17 and 19 of the same when the member is slid forward and rearward. As is better shown in FIGS. 3, 4 and 8, the slide member 59 comprises a resilient front tip 61 that is engaged by the hooks 51 of the ejector 43 when this ejector moves from a maximum forward position (see FIG. 8) to the rear. The slide member 59 also comprises a lower rib 63 that projects downwardly and is slidably engaged into the rear slot 19 of the chassis. It further comprises a rear edge 65.

Referring back to FIG. 2, the slide member 59 has an upper surface opposite to the lower rib 63, which comprises a front portion 67 of a first color (e.g. green), a medium portion 69 of a second color (e.g. white) and a rear section 71 of a third color (e.g. red).

An actuating button 73 is slidably mounted at the rear end 9 of the chassis 7 so as to be movable along the longitudinal axis of this chassis. This button 73 has a front surface 75 that extends close to the rear edge 65 of the slide member 59 when the shaft 27 is pushed rearwardly within the passage 15 and the leaf spring 63 is lockingly engaged with the stop 20 in the rear slot 19 in front of the lower rib 63 of the slide member 59 (see FIG. 4). This button is retained by a pair of L-shaped arms 74 slidably engaged into grooves made in retaining sidewalls provided at the rear end of the chassis 7 (see FIG. 2).

The actuating button 73 is also slidably mounted into a tubular safety shield 77 attached by a retaining ring 79 to the housing 81 at the rear end 9 of the chassis 7. As can be better seen by comparing FIGS. 4 and 5, the safety shield 77 is of such a length that only a meniscus 83 formed on a user's fingertip pressed onto the shield may push forward the actuating button 73 to such an extent as to cause the slide member 59 to disengage the leaf spring 33 and thus to fire the injector. Advantageously, the safety shield 77 has an internally chamfered rearward edge 85 (see FIGS. 3 and 5) to assist in raising the meniscus formed on the user's fingertip without requiring an undue amount of finger pressure.

Last of all, the lancet injector 1 comprises the housing 81 already mentioned hereinabove, which encloses all the above components except for the mouth 11 of the chassis and the shelf-defining ring 13 the knob 49 of the ejector 43, the safety shield 77 and the actuating button 73.

Figure 2:
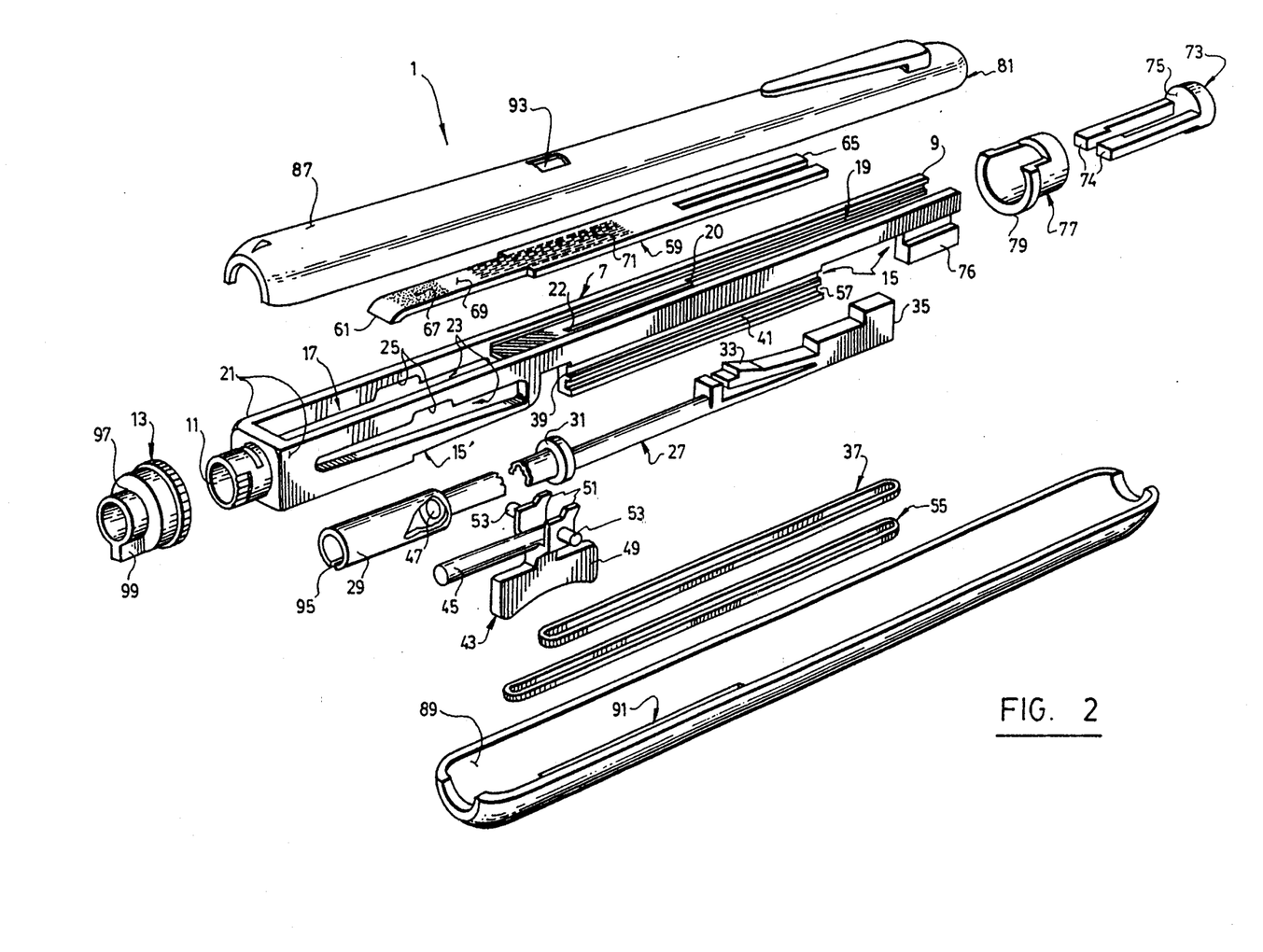
FIG. 2 is an exploded perspective view of the lancet injector shown in FIG. 1.

As is shown in FIG. 2, the housing 81 is preferably made of two clippable half-parts 87,89 that together form an elongated enclosure in which are located all the other components of the injector, except for the elements mentioned, hereinabove, including in particular the actuating button 73 and the knob 49 of the ejector 43 that slidably extends into an elongated opening 91 provided along the lower half-part 89.

A window opening 93 is provided in the upper surface of the slide member 59 and positioned with respect to the chassis 7 to allow the colored portions 67, 69 and 71 on the upper surface of the slide member to be displayed successively, as will be explained hereinafter.

As aforesaid, the above described lancet injector 1 is intended to be used with a lancet 3 and an isolating platform 5. Both of these components will now be described in greater details.

As is shown in FIGS. 1 and 9 to 12, the lancet 3 comprises an elongated body 101 made of plastic material, that is snugly insertable into the launching socket 29 of the lancet injector 1. The lancet 3 also comprises an axial needle 103 with a sharp end. The needle 103 is embedded into the body 101 except for its sharp end that projects out at a given distance away from one end 105 of the same.

As is clearly shown, the elongated body 101 comprises a plurality of longitudinal ribs 107 to make it easier to grasp and handle, and easier to mount and lock in the launching socket 29. For this purpose, one of these ribs 107 has a projection 109 that is sized and positioned to fit into a key slot 95 provided in the launching socket 29 so as to lock the lancet in a given radial position within this socket (see FIG. 1).

As is also clearly shown, the one end 105 of the body of the lancet where the sharp end of the needle 103 projects out, has a pair of radially extending sections 111 that project from the same in the same direction as the sharp end of the needle.

Referring now to FIGS. 1, 9 and 13 to 15, the isolating platform 5 which is intended to be used in combination with the lancet 3 and the lancet injector 1, comprises a front plate 113 that extends transversally to the mouth 11 of the chassis when the isolating platform is connected thereto. This plate 113 has a given thickness and a central through-hole 115 of a diameter smaller than the one of the body of the lancet, and more particularly of the one end 105 of this body, so as to stop the same while allowing the needle 103 of the lancet to pass through the through-hole 105 and to project out of the plate 113 when the injector 1 is fired.

The isolating platform 5 also comprises a fixation sleeve 117 coaxial to the front plate 113 and sized to snap onto the shelf-defining ring 13 that is coaxially mounted onto the mouth of the chassis, so as to detachably connect the isolating platform relative to this mouth 11.

As can be appreciated, proper selection of the thickness of the front plate 113 of the isolating platform 5 permits to adjust at will the depth of penetration of the sharp end of the needle 103 into the skin of the patient when the lancet injector 1 is fired.

As can be also appreciated, the isolating platform 5 may also, if desired, be detachably connected directly to the mouth 11 of the chassis, thereby avoiding the need for a shelf-defining ring 13. However, this will make the combination much less versatile, as only one depth of penetration corresponding to a given front plate thickness would then be provided.

Figure 9:
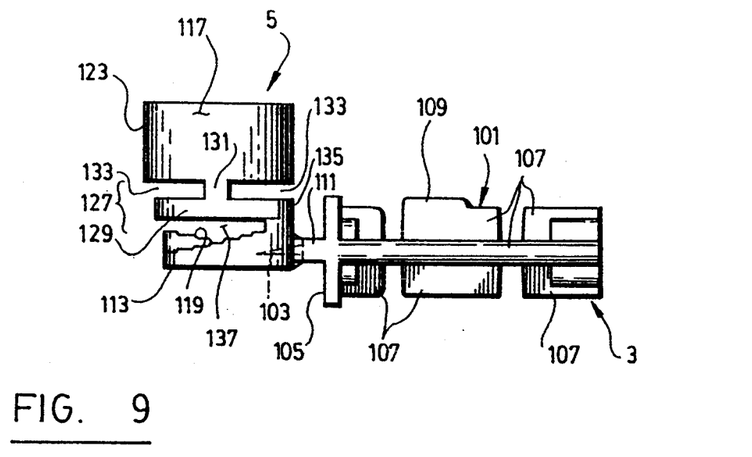
FIG. 9 is a side elevational view of he lancet already shown in perspective view in FIG. 1, showing the isolating platform molded at one end thereof to embed the needle and keep it sterile until it is used.
Figure 10:
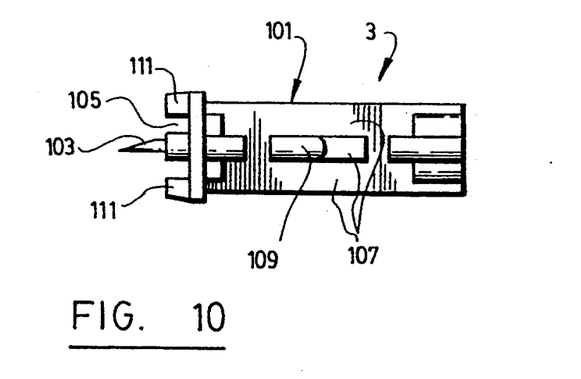
FIG. 10 is a top plan view of the lancet shown in FIG. 1.
Figure 11:
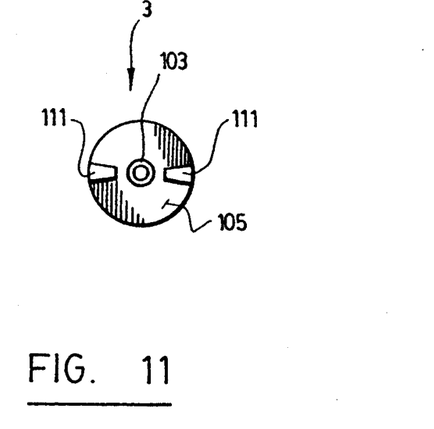
FIG. 11 is a front elevational view of the lancet shown in FIG. 1.
Figure 12:
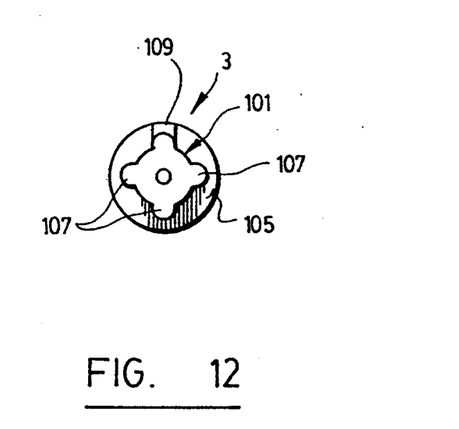
FIG. 12 is a rear elevational view of the lancet shown in FIG. 1.

The isolating platform 5 is advantageously made of the same plastic material as the lancet 3 and is moulded together to form an integral structure moulded onto the needle 103, with the body 101 of the lancet 3 radially projecting from the front plate 113 of the platform 3 as is shown in FIG. 9. In such a position, the body 101 and the front plate 113 are integrally connected by a very short stem of reduced diameter that is coaxial to the needle 103 and sized to make the isolating platform 5 easily detachable from the lancet 3 by twisting and pulling, to release the sharp end of the needle. This embodiment is particularly interesting since it permits to keep the sharp end of the needle 103 sterile until the lancet 3 is used.

Figure 15:
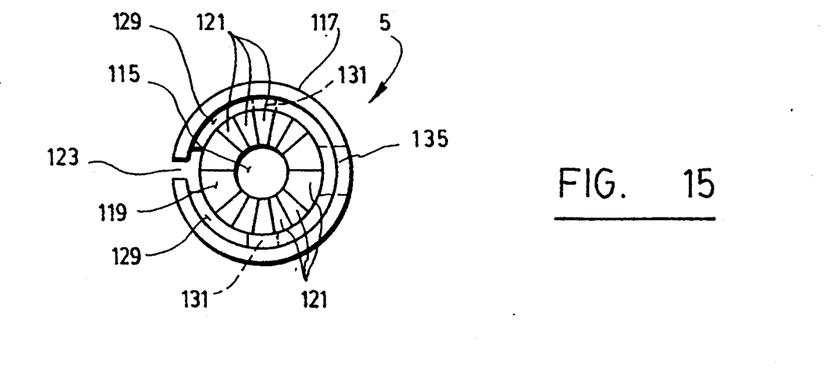
FIG. 15 is a rear elevational view of the platform showing FIG. 13.

As is better shown in FIGS. 9, 13 and 15, the front plate 113 of the isolating platform 5 has one surface 119 hereinafter called "inner surface", which faces the radially extending sections 111 of the body 101 when the lancet 3 is inserted in the launching socket 29 and the platform 5 is snapped onto the ring 13 mounted onto the mouth of the ejector 1. This inner surface 119 having at least two and preferably seven different pairs of radially opposite sections or steps 121 that project at different distances away from an average plane parallel to the plate 113.

As can now be understood, proper adjustment of the position of the isolating platform 5 by rotation of the same about the mouth 11 of the lancet injector relative to the lancet 3 when the same is inserted into the launching socket 29, allows the radially extending sections 111 projecting from the one end 105 of the body 101 of the lancet to be brought into alignment with a preselected pair of radially opposite sections 121 on the inner surface 119 of the front plate of the platform 5 and thus to control the depth of penetration of the lancet.

To facilitate this adjustment, the fixation sleeve 117 of the isolating platform 5 can be snapped onto a supporting shelf 97 forming part of the shelf-defining ring 13 that is coaxially and rotatably mounted onto the mouth 11 of the chassis in a manner known per se. Thus, proper rotation of the ring 13 about the longitudinal axis of the injector 1 causes the requisite adjustment of the position of the isolating platform 5 relative to the lancet 3.

Advantageously, the supporting shelf 97 of the ring 13 is provided with a longitudinal key 99 and the fixation sleeve 117 of the isolating platform 5 is in the form of a cylinder that is longitudinally slotted over its full length at 123 and is of such a diameter that it can resiliently be opened to snap onto the longitudinal key 99 of the ring 13. Moreover, the ring 13 and either the mouth 11 or the housing 81 can be provided with marks 125 (see FIG. 1) to allow the user to check the position of the platform 5 relative to the lancet 3 and thus to ascertain the maximum depth of penetration of the sharp end of the needle of the lancet when the injector is fired.

Figure 1:
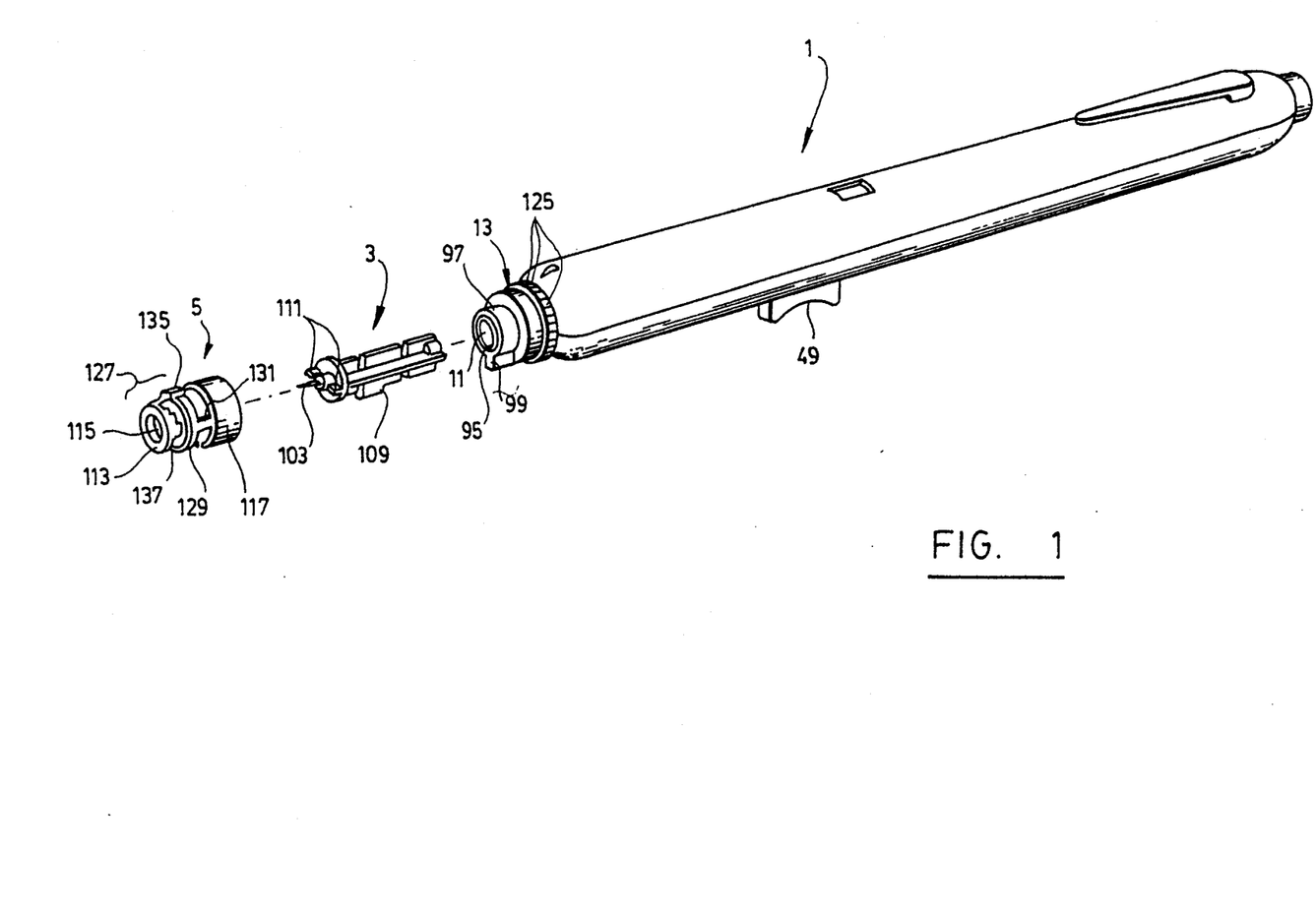
FIG. 1 is a front perspective view of a lancet injector according to the invention, showing the lancet and isolating platform intended to be used in combination therewith in their ready-to-install position.
Figure 13:
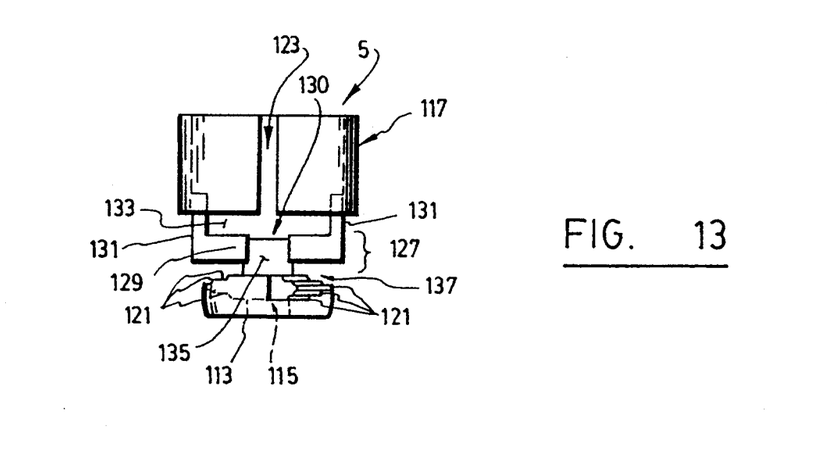
FIG. 13 is another side elevational view of the isolating platform already shown in FIGS. 1 and 9.
Figure 14:
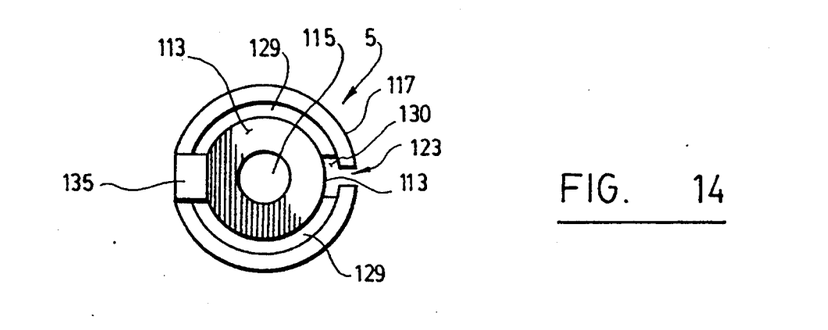
FIG. 14 is a front elevational view of the platform shown in FIG. 13.

As is better shown in FIGS. 1, 9 and 13, the isolating platform 5 further comprises a medium section 127 joining the front plate 113 to the slotted fixation sleeve 117. This medium section 127 comprises an open ring 129 which extends in a plane parallel to the one in which the plate 113 extends and whose opening 130 is aligned with the slot 123 in the sleeve 117. This open ring 129 has an inner diameter that is substantially equal to the outer diameter of the front plate 113 and is connected to the fixation sleeve 117 by means of two opposite tabs 131 that are symmetrically positioned with respect to the slot 123. The tabs 131 have inner surfaces that are slightly undercut relative to the inner surfaces of the adjacent sleeve 117 and ring 129. Both of them together with the adjacent sleeve 117 and ring 129, define a pair of opposite peripheral slots 133 that extend in a plane parallel to the one in which the open ring 129 extends. The open ring 129 is also connected to the front plate 113 by means a single tab 135 that is opposite to the slot 123 and opening 130. This single tab 135 together with the adjacent plate 113 and ring 129, define a large peripheral slot 137 that is parallel to the slots 133. The purpose of the slots 133 and 137 is to grip the body 101 of the lancet 3 and cause the plate 113 to hood the sharp end of the needle 103 when the lancet 3 is ejected, as will be better explained hereinafter.

The operation of the lancet injector according to the invention will now be described. However, prior to doing so, it is worth noting that the lancet injector 1 according to the invention includes eleven plastics components and two elastomeric bands having a total overall weight of about 1 oz. (28.5 grams). All these components are advantageously designed to either clip, slide, press or lock into the chassis 7 which, for quality purposes, can then be inspected and tested as a unit prior to enclosing it within the housing parts 87, 89 which dovetail clip together to complete the assembly. If ultimately desired for security, the two housing parts 87, 89 may be permanently ultrasonically welded and the inherent dovetails will at that time also serve as adequate energy concentrators for this purpose.

The sequential operation of the lancet injector 1 will be described with reference to FIGS. 3 to 8.

POSITION 1

Figure 3:
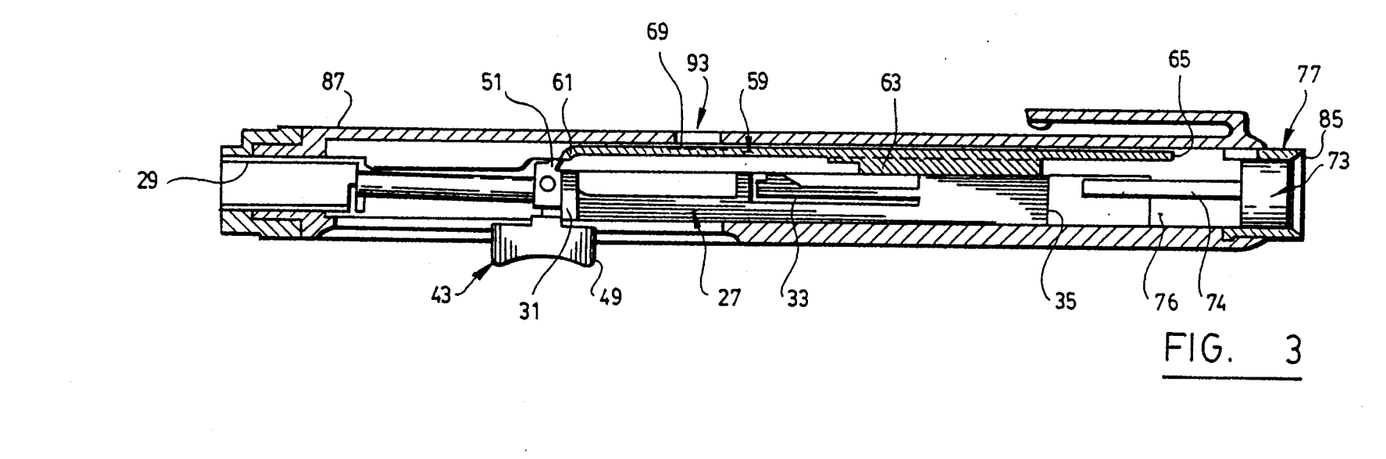
FIG. 3 is a cross-sectional, side elevational view of the lancet injector of FIGS. 1 and 2, in its ready-to-use position.

FIG. 3 shows the normal or rest position of the injector 1. At this stage, a previously used lancet has already been ejected and the injector 1 is ready for loading and cocking as confirmed by the white display made by the medium portion 59 of the slide member 59, which is visible through the window 93 in the housing part 87. The knob 49 of the ejector 43 can then be vertically depressed by thumb pressure to deflect the shaft 27 upwards, thereby causing it to be stopped by, the chassis 7 and thus restraining the shaft from moving rearward during the time a new lancet is being loaded into the launching socket 29. Standard lancets may be used if desired and loaded at any random radial angle. If variable depth lancets 3 according to the invention are used, they must be oriented during loading to insure that the lancet key 109 is located within the key slot 95 provided along the lower edge of the launching socket 29.

POSITION 2

Figure 4:
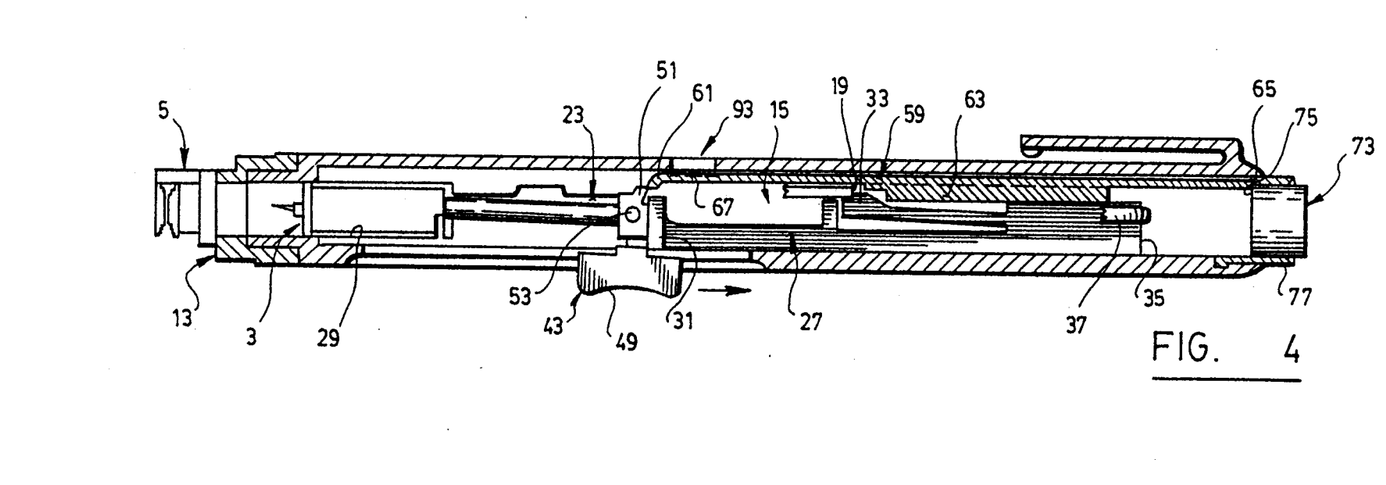
FIG. 4 is a view similar to FIG. 3, showing the lancet injector in locked position, with the lancet and isolating platform in operative position.

Then, the vertical thumb pressure is released and the thumb can be placed in front of the knob 49 of the ejector with pressure then applied rearward i.e. to the right in the drawings. Due to the angulated slots 23 provided in chassis 7, the ejector 43 whose pins 53 ride within the slots, is at that time in the cycle at an elevation at which it positively engages the extreme left-hand tip 61 of the slide member 59 as well as the shaft 27. Then, as is shown in FIG. 4, both the slide member 59 and the shaft 27 move to the right while helping to relay the same direction of motion to the safety button 73 which is finally tensioned rearward while the injector is armed by the elastomeric band 37. In so doing, the end face of the button 73 projects beyond the end of the safety shield 77. Simultaneously, the lower rib 63 situated on the underside of slide member 59 vacates the rear locking slot 19 rearward the stop 20 of the chassis 7, thus readying this slot 19 for the locking leaf spring 33 of shaft 27 which then drops into it behind the stop 20 and thus cocks the injector and arms the safety button 73. The slide member 59 in assuming its right-hand position, moves rearwards the front portion 67 of the slide member 59 and changes the color displayed in the window to green, indicating that the injector is cocked. The isolating platform 5 can be pressed onto the ring 13, then causing the sleeve 117 of the platform to expand and grip the shelf 97 of the ring. If use is made of a platform 5 of the variable depth type as was disclosed above (which should be used only with a variable depth type lancet), then the ring 13 may be rotated to select any of a number of e.g. seven click depth comfort graduations or marks 125 provided around the periphery of this ring. Alternatively, when used With a standard lancet (non-variable depth), a separate isolating platform of the non-variable type can be mounted onto the ring 13 in a similar manner although the graduation feature is then non-operative. During the time the platform 5 is being mounted, the safety button feature disclosed above ensures that the injector is not inadvertently discharged, thus obviating the danger of accidental finger-sticks.

POSITION 3

Figure 5:
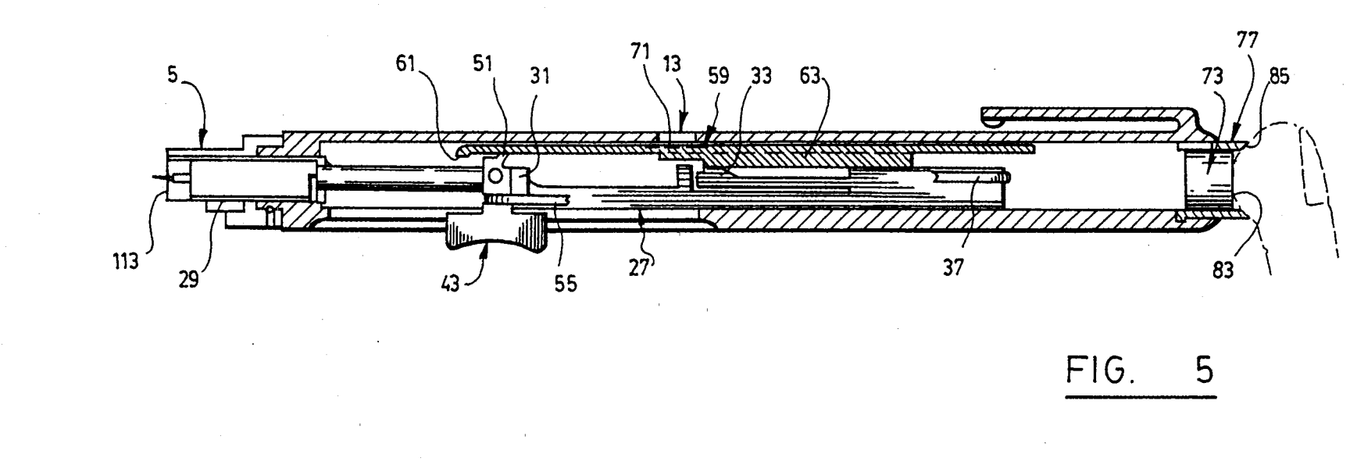
FIG. 5 is a view similar to FIG. 4, showing the lancet injector in fired position.

Next, the front plate 113 of the isolating platform 5 can be pressed against the skin of the patient and a deliberate finger pressure be applied to both the safety button 73 and its transparent shield 77. As is shown in FIG. 5, this causes a well defined meniscus 83 to form within this shield. The formation of the meniscus is greatly augmented by the internally chamfered edges 85 of the shield 83 which assist in raising the meniscus without requiring an undue or uncomfortable amount of finger pressure. As the meniscus 89 forms and increases in height, the safety button 73 is yet further depressed causing the slide member 59, to move forward and its lower rib 63 eventually to press upon the leaf-spring 33 of the shaft 27, thus expelling it from the rear slot in the chassis 3 and causing the injector to uncock and fire. In so doing, the lancet needle 103 passes through the through-hole 115 provided in the front plate 113 of the isolating platform 5 and pierces the skin to the desired depth. The coincident movement of the slide member 59 causes the window display to change to the rear portion 71 red in color and thus to give a visible warning that the injector now contains a used lancet which must be ejected as the next step. Upon firing, the kinetic energy stored by the elastomeric band 37 is released and considerable inertia is relayed to the slide member 59 which first moves forward in concert with the shaft 27. When said shaft ultimately becomes constrained by the other elastomeric band 55 via the ejector 43 bearing against the abutment 31, the slide member 59 which is not so constrained continues its forward movement by virtue of its stored inertia, thereby causing its tip 61 to flex and rise and then overtake the hook 51 of the ejector 43. The safety button 73 which has lost all tension and is no longer in contact with the slide 3 member 59 which controls the firing, is now disabled.

POSITION 4

Figure 6:
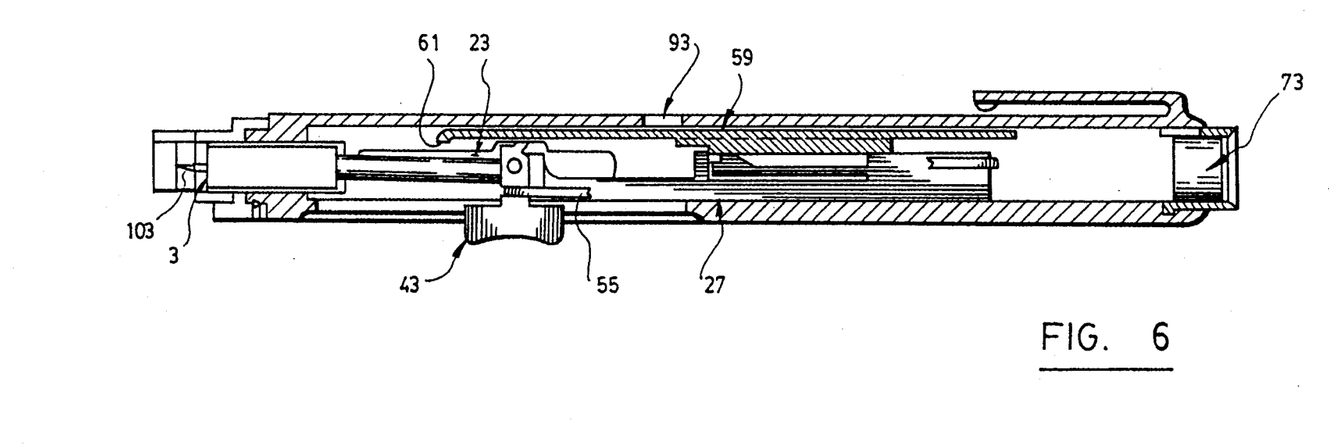
FIG. 6 is a view similar to FIG. 4, showing the lancet injector in retracted position after firing.

Then, the tension of the elastomeric band 55 withdraws the shaft 27 and with it the lancet 3 and its needle 103, as is shown in FIG. 6. The tip 61 of the slide member 59 is now to the left of the ejector 43 and the top face of said ejector 43 is currently height "programmed" by the angulated slots 23 in the chassis 7. As a result, the ejector 43 is completely clear of slide member 59 and any attempt to re-cock the used lancet in this fired and retracted position with be frustrated, as moving the ejector 43 to the right will have no effect upon the slide member, shaft 27 of safety button 73 which will remain motionless.

POSITION 5

Figure 7:
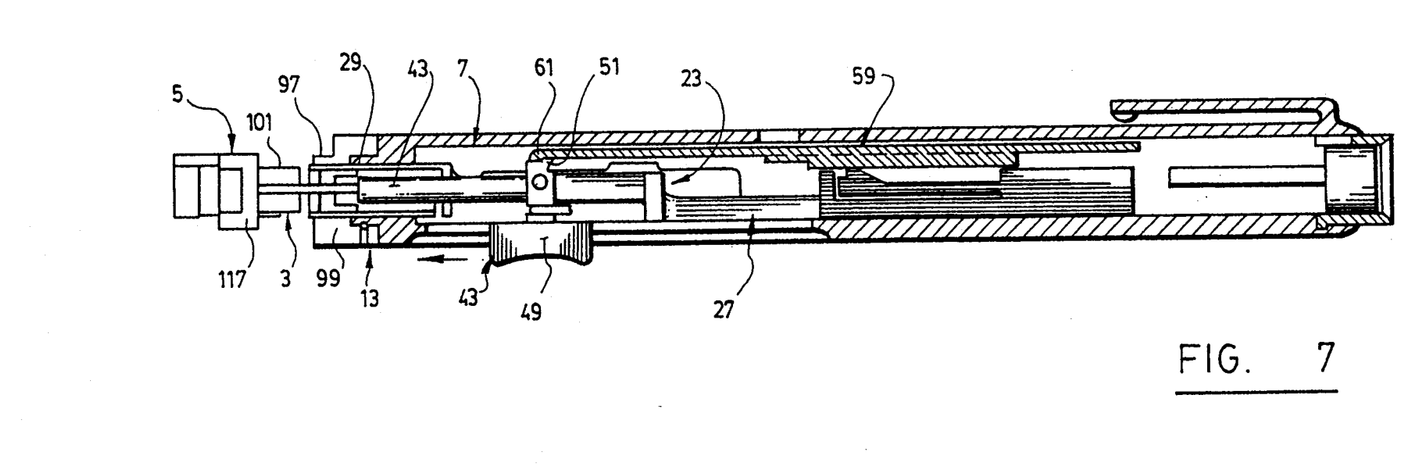
FIG. 7 is a view similar to FIG. 4, showing the lancet injector in the course of ejection of the used lancet.

To eject the lancet 3, thumb pressure can be applied behind the knob 49 of the ejector 43, causing it to move to the left whereupon it commences to eject the lancet 3, as is shown in FIG. 7. Simultaneously, the angulated slots 23 in the chassis 7 will cause the ejector 43 to gradually rise so that the sloping left-hand edges of the hook 51 of the ejector will eventually become sufficiently elevated to engage the right-hand sloping edge of the tip 61 of the slide member 59 which is drawn to the left. As the ejector 43 continues its movement as shown with the arrow, the lancet 3 is gradually expelled from the socket 29 at the end of the shaft 27, and starts to press upon the inner face of the isolating platform 5 causing said platform to be dislodged from the shelf 99 of the ring 13, whereupon the internal diameter of the fixation sleeve 117 of the platform which was stretched over the shelf 99 rapidly snaps to its original unstressed smaller diameter. The abrupt liberation of tension as the platform 5 finally escapes the edge of the shelf 99, propels the platform forward just as it is contracting to grip the lancet body 101, thus ensuring that the platform 5 is ahead of the end of the needle of the lancet 3, which it thus hoods and protects.

POSITION 6

Figure 8:
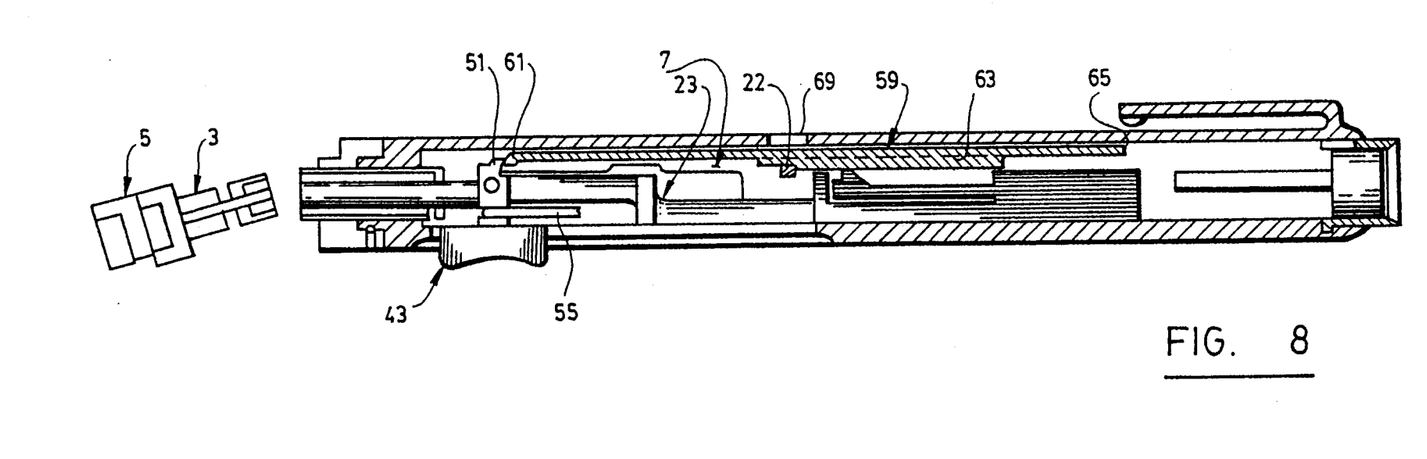
FIG. 8 is a view similar to FIG. 4, showing the lancet injector in its final position of ejection of the used lancet with its isolating platform.

Towards the end of its stroke, the ejector 43 dislodges the assembled lancet 3 and platform 5 in concert. If a standard lancet of the non-variable depth type is used together with a non-variable isolating platform, they will both be ejected, but unassembled. Then, the slide member 59 continues to be dragged to the left until the lancet 3 has been completely ejected. Immediately thereafter, its further movement becomes restrained by its lower rib 63 which hits the ends 22 of the rear slot 19 provided in the chassis 7 (see FIG. 2a). Due to the continuing movement of ejector 43 coupled with the restraint of the slide member 59 and by virtue of their sloping faces which are still in contact and also the angulated slots 23 in the chassis 7, vertical pressure is exerted upon the tip 61 of the slide member 59 which flexes upwards allowing the ejector 43 to overtake, snap beyond and thus firmly engage the slide member 59, as is shown in FIG. 8. Immediately when the thumb pressure is released, the ejector 43 which is under tension from the elastomeric band 55, pulls the slide member 59 rearward to its normal rest position and the color display in the window changes back to white as before. The complete cycle may then be repeated.

Therefore, in use, the following steps are carried out in this order.

i) The lancet injector 1 is loaded by manually inserting a lancet 3 into the launching socket 29 while pressing onto the knob 49 of the ejector 43 to deflect the adjacent shaft 27 to cause the pins 51 to engage the notches made in the angulated slots of the chassis and to be locked therein. This prevents the shaft 27 from moving rearward (see FIG. 3).

ii) Then, the injector 1 is cocked by pushing rearwards the knob 49 of the ejector 43 bearing on the abutment 31 of the shaft 27 so as to push rearwards this shaft 27 until its leaf spring 33 is lockingly engaged with the stop 20 in the rear slot 19 of the chassis, such pushing also causing the slide member 59 to move freely rearward behind the leaf spring engaged with the stop in the rear slot, and the first elastomeric band 37 to tension (see FIG. 4). It is worth noting that during this cocking step, the angulated slots 23 cause the lancet ejector 43 to move away from the front tip 61 of the slide member 59 and thus to avoid any interference with the same until the injector is fired.

iii) Next, the lancet injector 1 is fired by pressing forward onto the actuating button 73 such a pressing causing the slide member 59 to move forwards and its lower rib 63 to disengage the leaf spring 33 and thus to release the shaft 27 that is projected forwardly and then rearwardly rapidly under the action of the first and second elastomeric bands 37, 55. Such a movement in turn causes the lancet 3 in the launching socket 29 to move out of the mouth of the chassis to hit the isolating platform 5 and the lancet needle to penetrate for a very short period of time in the skin of a patient bearing onto the isolating platform 5 (see FIG. 5). It is worth noting that during the firing step, the angulated slots 23 cause the lancet ejector 43 to move toward the front tip 61 of the slide member 59 and its hook 51 to engage this front tip rearwardly of the same and to push the slide member 59 forwards.

iv) Finally, the lancet 3 can be ejected from the ejector 1 by pushing forwards the lancet ejector 43 until the lancet 3 falls out of the mouth of the chassis 7, the ejector 43 and the slide member 59 hooked by the same being then moved back to step (i) under the action of the second elastomeric band 55. During this ejecting step, the angulated slots cause the hook 51 of the ejector to deflect the front tip 61 of the slide member 59 and to pass in front of the same, thereby causing the ejector to push back the slide member 49 when it moves rearwards under the action of the second elastomeric band.

It is further worth noting that:

when the lancet injector 1 is in its loading position in step (i), the second color (i.e. white) is displayed through the window 93;

when the lancet injector 1 is in locked position at the end of step (ii), the first color (i.e. green) is displayed through the window 93; and when the lancet injector has been fired but the lancet 3 has not been ejected yet in step (iii), the third color (i.e. red) is displayed through the window.

As aforesaid, the structure of the isolating platform 5, and more particularly its resilient fixation sleeve 117, provides for the automatic acceleration of the platform 5 relative to any given speed of the lancet 3, when the lancet 3 makes a first contact with the platform in order to complete the ejection action. Such an automatic acceleration causes the platform 5 to leap ahead of the lancet body 101 and of the sharp end of the needle 103 prior to snapping closed onto the lancet 3 to which it when becomes adequately attached, thus obviating accidental needle-sticks.

In practice, the differential between the acceleration speeds of the lancet 3 and the platform 5 is provided by virtue of the dissipation of the kinetic energy previously stored as potential energy within the resilient fixation sleeve 117 of the platform due to it being stretched over and onto the supporting shelf 97 of the rotatable ring 14. Such a stretching serves three distinct purposes, namely:

(1) to securely affix the platform 5 to the injector 1 prior to and during the injection process;

(2) to enlarge the internal diameter of the two gripping slots 133, 137 so that they do not obstruct the lancet during the injection action; and (3) to provide a potential energy storage means whose energy is subsequently dissipated in the form of kinetic energy imparted to the platform 5 as the fixation sleeve 113 slides off the supporting shelf 97 at an angle, thus accelerating the platform 5 at an increased forward velocity relative to the lancet body.

Thus, the platform 5 upon leaving the shelf 97, will rapidly accelerate and jump ahead of the needle tip prior to locking upon the body 101 of the lancet.

What is claimed is:

1. A lancet injector for use with a lancet and an isolating platform through which said lancet passes when it is projected by said injector, said lancet injector comprising:

(a) an elongated chassis having:
   a longitudinal axis extending between a front end and a rear end;
   wherein the front end is open forming a mouth on which said isolating platform can be detachably fixed;
   said chassis defining an elongated passage opening into said mouth and comprising a longitudinal front slot and a longitudinal rear slot both opening into said passage, said slots being aligned, (b) a shaft slidably mounted in a non-rotatable manner within said passage, said shaft having:
   a forward end integrally connected to a launching socket in which the lancet to be injected is detachably insertable;
   a first abutment at a first distance rearward the launching socket;
   a leaf spring at a second distance rearward the first abutment, said leaf spring projecting forwardly outwardly from said shaft and being lockingly engageable within a stop made in the rear slot of the chassis when said shaft is moved rearwardly within the passage; and
   a rearward end defining a second abutment;

(c) a first elastomeric band held under slight tension between the second abutment of the shaft and a first elastomeric band attachment point provided on the chassis rearward the mouth;

(d) a lancet ejector slidably mounted in a nonrotatable manner within the passage of the chassis between the mouth and the first abutment of the shaft, said ejector comprising:
   a forwardly projecting stem that is slidably movable within the launching socket through a rear opening provided in the launching socket;
   an operating knob projecting out of said chassis through an elongated opening provided in the chassis opposite to said front slot; and
   a small hook opposite to the knob, said hook being slidably engageable into said front slot of the chassis, (e) a second elastomeric band held under slight tension between the lancet ejector and a second elastomeric band attachment point provided on the chassis forward the chassis rear end;

(f) a slide member slidably mounted onto the chassis so as to extend longitudinally over the front and rear slots of said chassis when said member is slid forward and rearward, said slide member comprising;
   a resilient front tip that is engaged by the hook of the ejector when said ejector moves from a maximum forward position to the rear;
   a lower rib that projects downwardly and is slidably engaged into the rear slot of the chassis; and
   a rear edge, (g) an actuating button slidably mounted at the rear end of the chassis so as to be movable along the longitudinal axis of said chassis, said button having a front surface that extends close to the rear edge of the slide member when the shaft is pushed rearwardly within the passage and the leaf spring is lockingly engaged with the stop in the rear slot in front of the lower rib of said slide member, and (h) a housing enclosing all the above components except for the mouth of the chassis, the knob of the ejector and the actuating button;

whereby, in use, one may carry out the following steps:

i) loading the lancet injector by manually inserting the lancet into the launching socket while pressing on the know of the ejector to deflect the adjacent shaft and thus prevent it from moving rearward;

ii) cocking said injector by pushing rearwards the know of the ejector bearing on the abutment of the shaft so as to push rearwards said shaft until its leaf spring is lockingly engaged with the stop in the rear slot of the chassis, such pushing also causing the slide member to move freely rearward behind the leaf spring engaged with the stop in the rear slot, and the first elastomeric band to tension;

iii) firing said injector by pressing forward onto the actuating button, such pressing causing the slide member to move forward and its lower rib to disengage the spring and thus to release the shaft that is projected forwardly and then rearwardly rapidly under the action of the first and second elastomeric bands, such a movement causing in turn the lancet in the launching socket to move out of the mouth of the chassis past the isolating platform and to penetrate for a very short period of time in the skin of a patient bearing onto said isolating platform; and iv) ejecting the lancet from said injector by pushing forward the lancet ejector until the lancet falls out of the mouth of the chassis, said ejector and the slide member hooked by the same being then moved back to step (i) under the action of the second elastomeric band.

2. The lancet injector of claim 1, wherein:
the chassis (a) has two opposite sidewalls that extend bilaterally and symmetrically on both sides of the longitudinal front slot and elongated opening of said chassis, each of said sidewalls comprising an angulated slot that extends forwardly at a sight angle towards said front slot said angulated slot being of substantially the same length as said front slot and being provided with a notch at substantially mid-length, that extends in a direction opposite to said elongated opening; and the lancet ejector (d) comprises two opposite pins that extend transversally to the stem and are slidably engaged into the angulated slots of the chassis, respectively, whereby:

during the loading step (i), the pressure exerted on the knob causes the pins to engage the notches made in the angulated slots of the chassis and to be locked therein;

during the cocking step (ii), the angulated slots cause the lancet ejector to move away from the front tip of the slide member and thus to avoid any interference with the same until the injector is fired;

during the firing step (iii), the angulated slots cause the lancet ejector to move toward the front tip of the slide member and its hook to engage said front tip rearwardly of the same and to push said slide member forwards; and during ejecting step (iv), the angulated slots cause the hook of the ejector to deflect the front tip of the slide member and to pass in front of the same, thereby causing said ejector to push back the slide member when it moves rearwards under the action of the second elastomeric band, whereby one must necessarily eject the lancet contained in the injector when said lancet has been used before said injector can be cocked again.

3. The lancet injector of claim 1, wherein the actuating button (g) is slidably mounted into a tubular safety shield attached to the housing at the rear end of the chassis, said safety shield being of such a length that only a meniscus formed on a user's fingertip pressed onto said shield, may push the actuating button to such an extent as to cause the slide member to disengage the leaf spring and thus to fire the injector.

4. The lancet injector of claim 3, wherein said safety shield has an internally chamfered rearward edge to assist in raising the meniscus formed on the user's fingertip without requiring undue amount of finger pressure.

5. The lancet injector of claim 3, wherein:

the slide member (f) has an upper surface opposite to said lower rib which comprises a front portion of a first color, a medium portion of a second color and a rear section of a third color; and the housing (h) has a window opening onto the upper surface of the slide member and positioned with respect to said chassis so that:

when the lancet injector is in its loading position in step (i), the second color is displayed through said window;

when the lancet injector is in locked position at the end of step (ii), the first color is displayed through the window; and when the lancet injector has been fired but the lancet has not been ejected yet in step (iii), the third color is displayed through the window.

6. The lancet injector of claim 5, wherein the housing (h) is made of two clippable half-parts that form together an elongated enclosure in which are located all the other components of the injector, except for the mouth of the chassis the actuating button and the knob of the ejector (d) that slidably extends into an elongated opening provided along one of said half-parts.

7. The lancet injector of claim 3, wherein the housing (h) is made of two clippable half-parts that form together an elongated enclosure in which are located all the other components of the injector, except for the mouth of the chassis, the actuating button and the knob of the ejector (d) that slidably extends into an elongated opening provided along one of said half-parts.

8. The lancet injector of claim 1, wherein:

the slide member (f) has an upper surface opposite to its lower rib, which comprises a front portion of a first color, a medium portion of a second color and a rear section of a third color; and the housing (h) has a window opening onto the upper surface of the slide member and positioned with respect to said chassis so that:

when the lancet injector is in its loading position in step (i), the second color is displayed through said window; when the lancet injector is in locked position at the end of step (ii), the first color is displayed through the window; and when the lancet injector has been fired but the lancet has not been ejected yet in step (iii), the third color is displayed through the window.

9. The lancet injector of claim 8, wherein the housing (h) is made of two clippable half-parts that form together an elongated enclosure in which are located all the other components of the injector, except for the mouth of the chassis, the actuating button and the knob of the ejector (d) that slidably extends into an elongated opening provided along one of said half-parts.

10. The lancet injector of claim 1, wherein the housing (h) is made of two clippable half-parts that form together an elongated enclosure in which are located all the other components of the injector, except for the mouth of the chassis, the actuating button and the knob of the ejector (d) tibet slidably extends into an elongated opening provided along one of said half-parts.

11. The combination of a lancet injector as claimed in any one of claims 1 to 10 with a lancet and an isolating platform through which said lancet passes when it is projected by said injector, wherein:

(j) said lancet comprises:

an elongated body of a given diameter that is snugly insertable into the launching socket of the lancet injector; and an axial needle embedded into said body, said needle having a sharp end projecting out of said body at a given distance away from one end of the same; and (k) said isolating platform comprises:

a front plate that extends transversally to the mouth of the chassis when said isolating platform is connected thereto, said plate having a given thickness and a central through-hole of a diameter smaller than the one of the body of the lancet so as to stop said body while allowing the needle of the lancet to pass through the through-hole and to project out of said plate when the injector is fired; and a fixation sleeve coaxial to the plate and sized to snap onto the mouth of the chassis so as to detachably connect said isolating platform to said mouth;

whereby, by properly selecting the thickness of the plate of the isolating platform, one may adjust the depth of penetration of the sharp end of the needle into the skin of the patient when the lancet injector is fired.

12. The combination of claim 11, wherein:

the one end of the body of the lancet where the sharp end of the needle projects out, has at least one radially extending section that projects from said one end in the same direction as the sharp end of the needle; and the front plate of the isolating platform has an inner surface, that faces said at lest one radially extending section of the body when the lancet is inserted in the launching socket and the platform is snapped onto the mouth of the ejector, said inner surface having at least two different radial sections that project at different distances away from an average plane parallel to said plate;

whereby proper adjustment of the position of the isolating platform by rotation of the same about the mouth of the lancet injector relative to the lancet when the same is inserted into the launching socket, allows each radially extending section projecting from the one end of the body to be brought into alignment with a preselected radial section of the inner surface of the front plate of the platform and thus to control the depth of penetration of said lancet.

13. The combination of claim 12, wherein:

the elongated body of the lancet has at least one longitudinal rib;

said at least one rib is sized and positioned to fit into a key slot provided in the launching socket so as to lock the lancet in a given position within said launching socket;

a ring defining a supporting shelf is coaxially and rotatably mounted onto the mouth of the chassis; and the fixation sleeve of the isolating platform is snappable onto the supporting shelf of the ring to detachably connect said platform to the mouth of the injector;

whereby proper rotation of the ring about the longitudinal axis of the injector causes the requested adjustment of the position of the isolating platform relative to the lancet.

14. The combination of claim 13, wherein:

the supporting shelf of the ring is provided with a longitudinal key; and the fixation sleeve of the isolating platform is in the form of a cylinder that is longitudinally slotted over its full length and is of such a diameter that it can be resiliently opened to snap onto the longitudinal key of the ring.

15. The combination of claim 14, wherein the ring and mouth are provided with marks allowing a user to check the position of the platform relative to the lancet and thus to ascertain the maximum depth of penetration of the sharp end of the needle of the lancet when the injector is fired.

16. The combination of claim 15, wherein the isolating platform also comprises a medium section in the form of an open ring connected by small tabs to the front plate and to the fixation sleeve respectively, said open ring extending in a plane parallel to the front plate and defining with thee same and with the fixation sleeve a set of gripping slots, whereby, in use, when the lancet is to be ejected, forward motion of said lancet pushed by the stem of the ejector causes the isolating platform to be projected out of the shelf of the ring and to leap ahead of the lancet body and the sharp end of the needle by virtue of the dissipation of the kinetic energy previously stored within the resilient fixation sleeve due to it being stretched over and onto the supporting shelf, the so-projected platform then snapping onto the lancet which remains locked into the gripping slots, thereby obviating accidental needle-sticks and preventing the same lancet to be used more than once, either intentionally or accidentally.

* * * * *